United States Patent
Vallespi et al.

(10) Patent No.: US 6,632,793 B1
(45) Date of Patent: Oct. 14, 2003

(54) IMMUNOLOGICAL ACTIVITY FOR A PEPTIDE OF THE LIMULUS ANTI-LPS FACTOR

(75) Inventors: Maribel Guerra Vallespi, Havana (CU); Manuel de Jesus Arana Rosianz, Havana (CU)

(73) Assignee: Centro de Ingenieria Genetica y Biotecnologia, Havana (CU)

( * ) Notice: Subject to any disclaimer, the term of this patent is extended or adjusted under 35 U.S.C. 154(b) by 0 days.

(21) Appl. No.: 09/691,500

(22) Filed: Oct. 18, 2000

Related U.S. Application Data

(62) Division of application No. 09/160,309, filed on Sep. 25, 1998, now Pat. No. 6,191,114.

(30) Foreign Application Priority Data

Sep. 29, 1997 (CU) .............................................. 106/97

(51) Int. Cl.[7] .............................................. A61K 39/39
(52) U.S. Cl. ...................... 514/13; 424/278.1; 530/326
(58) Field of Search .......................... 514/13; 530/326; 424/278.1

(56) References Cited

FOREIGN PATENT DOCUMENTS

| WO | WO 92 20715 A | 11/1992 |
|---|---|---|
| WO | WO 95 65393 A | 2/1995 |

OTHER PUBLICATIONS

Battafaraono, R.J. et al., "Peptide Dervatives of Three Distinct Lipoplysaccharide Binding Proteins Inhibit Lipopolysaccharide–Induced Tumor Necrosis Factor–Alpha Secretion In Vitro," *Surgery*, 118(2):318–324 (Abstract) (1995).

Hoess, A. et al., "Crystal Structure of an Endotoxin–Netralizing Protein From the Horseshoe Crab, Limulus Anti–LPS Factor; at 1.5 A Resolution," *EMBO J.*, 12(9):3351–3356 (Abstract) (1993).

Ried, C. et al., "High Affinity Endotoxin–Binding and Neutralizing Peptides Based on the Crystal Structure of Recombinant Limulus Anti–Lipopolysacchlaride Factor," *J. Biol. Chem.*, 271(45): 28120–28127 (Abstract) (1996).

Roth, R.I. et al., "Limulus Antipopolysaccharide Factor Prevents Mortality Late in the Course of Endotoxemia," *J. Infec. Dis.*, 177:388–394 (1998).

*Primary Examiner*—Michael Borin
(74) *Attorney, Agent, or Firm*—Hoffmann & Baron, LLP

(57) ABSTRACT

The present invention relates a novel immunological effect of one peptide from Limulus anti-LPS factor protein. The immunological effect are, (1) Induce an antiviral state in both the Hep-2 and MDBK cell lines, (2) Supernatant from human mononuclear cells stimulated with peptide Limulus anti-LPS factor (LALF) is able to induce antiviral effect on Hep-2 cell line by mean of IFN-γ (3) LALF peptide is able to modulate the immune response in vitro and in vivo. The present invention can be used in therapeutic and/or prophylactic treatment regimens of humans and animals to enhance their immune responses, without stimulating the production of certain biochemical mediators (e.g., TNF-α) that can cause detrimental effects, such as fever and inflammation.

1 Claim, 7 Drawing Sheets

FIG. 1  CHYRIKPTFRRLKWKYKGKFWC

IMMUNOLOGICAL ACTIVITY FOR A PEPTIDE OF THE LIMULUS ANTI-LPS FACTOR

This application is a divisional application of U.S. Ser. No. 09/160,309 filed Sep. 25, 1998, now U.S. Pat. No. 6,191,114.

Despite aggressive management, septic shock arising from Gram-negative sepsis continues to be a leading cause of death in both surgical and medical patients. Death in such patients usually results from cardiovascular collapse and/or multiple organ system failure. One of the main components of Gram-negative bacterial thought to play an integral role in causing septic shock is an outer wall constituent, endotoxin (LPS).

Endotoxins are high molecular weight complexes, associated with the outer membrane of Gram-negative bacteria that produce pyrogenic reactions upon intravenous administration. Endotoxin is shed from living bacteria and is also released into the environment when bacteria die and decompose.

Bacterial endotoxin is a complex consisting of lipid, carbohydrate and protein. It is characterized by an overall negative charge, heat stability and high molecular weight. Highly purified endotoxin does not contain protein, and is a lipopolysaccharide (LPS).

Bacterial endotoxins are known to have profound biological effects in animals and humans, and to cause severe medical problems when present. Symptoms include induction of high fever, activation of complement and cytokine cascade and hypotension. It is critical to avoid endotoxin contamination in any pharmaceutical product or medical device, which come into contact with body fluids. High endotoxin levels in sera due to bacterial diseases, such as septicemia, are not easily treated. Antibiotic treatment of the infection only kills the bacteria, leaving the endotoxin from their cell walls free to cause fever.

LPS is an important mediator in the pathogenesis of septic shock and is one of the major causes of death in intensive-care units in the United States. It has been observed that exposure to LPS during sepsis stimulates an immune response in monocytes and macrophages that results in a toxic cascade resulting in the production of TNF-α and other proinflammatory cytokines. Morrison and Ulevitch, Am. J. Pathol., 93:527 (1978). Endothelial damage in sepsis probably results from persistent and repetitive inflammatory insults. Bone, *Annals Int. Med.* 115:457 (1991).

Several proteins have been investigated for their ability to bind and neutralize LPS and the potential use in the septic shock treatment. Among the most extensively studied of the LPS-binding proteins is bactericidal/permeability-increasing protein (BPI), a basic protein found in the azurophilic granules of polymorphonuclear leukocytes. The BPI protein from human PMNs has potent bactericidal activity against a broad spectrum of Gram-negative bacteria. This antibacterial activity appears to be associated with the amino terminal region (amino acids residues 1–199) of the isolated human BPI protein. Recently it has been shown that the N-terminal fragment of BPI (rBPI$_{25}$) neutralizes endotoxin activities and inhibits LPS-induced events in neutrophiles and macrophages. Helene et al., *Infection and Immunity*. 62:1185 (1994). In addition to its bactericidal effects, BPI has been shown to neutralize the toxic and cytokine-inducing effects of LPS to which it binds. Xoma Corporation is building a portfolio of therapeutic products based on BPI protein. The company's lead BPI-derived product, Neuprex, is in clinical efficacy trials for four indications: [1] Meningococcemia, [2] Hemorrhagic trauma, [3] Partial hepatectomy, [4] Severe intro-abdominal infections. XOMA Corporation Jul. 30, 1996.

Lipopolysaccharide binding protein (LBP) is a 60 kD glycoprotein synthesized in the liver, which shows significant structural homology with BPI. Shumann et al. Disclose the amino acid sequences and encoding cDNA of both human and rabbit. Like BPI, LBP has a binding site for lipid A and binds to the LPS from rough and smooth form bacterial. Unlike BPI, LBP does not possess significant bactericidal activity, and it enhances (rather than inhibits) LPS-induced TNF production. Schumann et al., *Science*, 249:1429 (1990).

One of the normal host effector mechanisms for clearance of bacteria involves the binding to and subsequent phagocytosis by neutrophils and monocytes. As part of this process, bacteria are exposed to bactericidal and bacteriostatic factor, including oxygen radicals, lysosomal enzymes, lactoferrin and various cationic proteins. LBP opsonizes LPS-bearing particles and intact Gram-negative bacteria, mediating attachment of these LPB-coated particles to macrophages. Wright et al., *J. Exp. Med.* 170: 1231 (1989). The attachment appears to be through the CD14 receptor of monocytes, which bind complexes of LPS and LBP. Wright et al. *Science* 249: 1431 (1990). Interaction of CD14, which is present on the surface of polymorphonuclear leukocytes as well as monocytes, with LPS in the presence of LBP has been shown to increase the adhesive activity of neutrophils. Wright et al., *J. Exp. Med.* 173: 281 (1991), Worthen et al., *J. Clin. Invest.* 90: 2526 (1992). Thus, while BPI has been shown to be cytotoxic to bacteria and to inhibit proinflammatory cytokine production stimulated by bacteria, LBP promotes bacterial binding to and activation of monocytes through a CD14-dependent mechanism. Novel biologically active lipopolysaccharide binding protein (LBP) derivatives including LBP derivative hybrid proteins which are characterized by the ability to bind to and neutralize LPS and which lack the CD14-mediated immunostimulatory properties of holo-LBP. Gazzano-Santoro, WO 95/00641. Moreover, peptides corresponding to residues 91–108 of LBP protein were identified that specifically bound the lipid A with high affinity. The peptides inhibited binding of LPS to LBP, inhibited the chromogenic Limulus amebocyte lysate reaction, and blocked release of TNF following LPS challenge both in vitro and in vivo, Taylor[24] et al., J. of Biol. Chem. 270: 17934, (19951.

Another LPS-binding proteins capable to bind and neutralize the endotoxin have been isolated from a horseshoe crab such as *Limulus polyphemus* and *Tachypleus antilipopolysaccharide* factor (TALF) isolated from *Tachypleus tridentatus*, Kloczewiak[29] et al., J. Infect. Dis. 170: 1490–7 (1994). . The cells from their hemolymph (amebocytes) undergo a complex series of biochemical reactions resulting in clot formation, analogous to mammalian blood coagulation. This phenomenon has been exploited in the form of bioassays sensitive to very low endotoxin levels.

Currently, a bioassay of this type is the method of choice for monitoring pharmaceutical manufacturing and is termed Limulus Amebocyte Lysate (LAL). Wainwright et al., WO 92/20715 relates the invention to the pharmaceutical utility of the endotoxin binding/neutralizing protein and disclose the use of the endotoxin binding/neutralizing protein for an endotoxin assay. It is yet another object of the invention to provide pharmaceutical compositions capable of binding and neutralizing endotoxin in vivo and containing therein an endotoxin binding/neutralizing protein corresponding at least to part of the endotoxin binding and neutralizing domain of the endotoxin binding/neutralizing protein isolated from a horseshoe crab in accordance with the invention.

Limulus anti-LPS factor (LALF) have been investigated for use in sepsis. Warren et al., *Infect.Immun.* 60: 2506–2513 (1992) and Garcia[25] et al., Crit. Care. Med. 22: 1211 [1994]. This protein is almost certain to suffer the disadvantages associated with other foreign proteins for human therapy, it is immunogenic and has only a shart half-life in circulation. These factors will reduce its clinical potential. None of these substances have been proven to be effective for the treatment of the serious conditions associated with Gram-negative infection in humans.

The solution to the above technical problem was achieved by providing substances, which relate to peptides, which bind tightly to LPS, and therefore have utility in the diagnosis and treatment of Gram-negative and other septic conditions. Battafaraono et al., synthesized three peptides from BPI, LALF, LBP (each 27 amino acid in length) of the proposed LPS-binding motif for these proteins. All small peptides derived from BPI, LALF and LBP retained significant endotoxin-neutralizing and bactericidal activity against many different gram-negative bacterial in vitro Battafaraono[26] et al., Surgery 118: 318–24 [1995]. More recently, Fletcher et al., designed a novel peptide-IgG conjugate, CAP-18 (106–138)-IgG, it binds and neutralizes endotoxin and kills gram-negative bacteria. Fletcher[27] et al., J. Infect. Dis. 175: 621–32 [1997].

Hoess et al., WO 95/05393 relates the invention to substances which bind with high affinity to endotoxin (lipopolysaccharide [LPS]), and which are useful for the prevention or treatment of, for example, Gram-negative and Gram-positive bacterial sepsis, and for the treatment of bacterial and fungal infections as well as for neutralizing effects associated with heparin. The substances are LPS-binding peptides comprising an LPS-binding domain. A peptide comprising the amino acids$_{31-52}$ from Limulus anti-LPS factor (LALF) was disclosed.

The crystal structure of LALF reveals a simple tertiary fold, which has a striking shape and amphipathicity. A surface-extended loop in the LALF structure (loop of LALF or LALF-loop) has similar features to polymyxin B by being positively charged and amphipathic and having several exposed hydrophobic and aromatic residues. Furthermore, the loop of LALF is distinguished by an alternating series of positively charged and hydrophobic/aromatic residues that, by virtue of the extended β-conformation, point in opposite directions, and a single pair of positive charges, that, because of the β-turn conformation, point in the same direction and maintain the amphipathicity. The loop contains no negatively charged amino acids. Hoess had described the minimal requirements of rLALF for endotoxin and lipid A with linear 10-mer peptides. Cyclic peptides, however, bind lipid A and endotoxin with high affinity, presumably by mimicking the three dimensional characteristics of the exposed hairpin loop, Ried[28] et al., J. Biol. Chem. 271: 28120–7 [1996]. The cyclic peptide LALF$_{36-47}$ is able to blocks TNF induction after endotoxin challenge in mice. Most recently have been described that Limulus antilipopolysaccharide factor (LALF) neutralize bacterial endotoxin and protect mice from LPS lethality even when LALF is administered long after the onset of continuous endotoxemia, Roth[31] RI. Su D H. Child A H. Wainwright N R and Levin J. Journal of Infectious Diseases. 177 (2): 388–394, 1998.

A similar amphipathic loop exists in three other proteins which bind LPS: rabbit and human lipopolysaccharide-binding protein (LBP) and human bactericidal/permeability-increasing protein (BPI). Inspection of the LBP and BPI sequences reveals a similar pattern of alternating residues that could produce an amphipathic loop.

However, these inventions do not reveal anything about the antiviral effect and/or activation of monocytes of either the endotoxin binding/neutralizing protein from *Limulus polyphemus* or the peptide comprising the amino acids$_{31-52}$ (SEQ ID NO: 1) from the protein. The use or therapeutic effectiveness in sepsis and infectious diseases are related with the LPS-binding. Furthermore, none of the references disclose the use of the peptide$_{31-52}$ (SEQ ID NO: 1) from Limulus anti-LPS factor for an antiviral treatment or to enhance the immune response.

It is known that viruses are small infectious agents that contain only one type of nucleic acid in its genome (RNA or DNA), generally as a sole molecule. Viruses replicate only in living cells and in man they may produce different diseases.

A. Generalized diseases where the virus is disseminated throughout the body as in small pox, yellow fever, dengue, etc.
B. Diseases of the nervous system as in poliomyelitis, aseptic meningitis caused by the intestinal viruses (polio, coxsackie), rabies, encephalitis transmitted by arthropods, etc.
C. Diseases of the skin or mucose: Herpes simplex, type I (usually of the mouth) and type II (usually genital).
D. Ocular diseases: Conjunctivitis due to adenovirus, conjunctivitis due to the Newcastle virus, epidermal hemorrhagic conjunctivitis.
E. Diseases of the liver: Type A Hepatitis (infectious hepatitis), type B hepatitis (hepatitis through the serum), etc.

Given that the viruses are necessarily intracellular parasites, the antiviral agents should be capable of selectively inhibiting the viral functions without damaging the host. There are several compounds that inhibit the virus in a specific way without affecting cellular metabolism, for example the amantadine, a synthetic amine that inhibits the virus A of the influenza; metisazone, an inhibitor of many pox viruses, the trifluorotimidine has been used with success in the treatment of lesions of the cornea due to the Herpes simplex virus. Many of these agents are acting as antimetabolites have the handicap that they are toxic to man.

Also tested because of their antiviral capacity and immune system stimulating ability in animals and man are compounds such as Levamisol and Isoprinosine, these agents are not antimetabolites, but stimulators of cellular immunity.

The interferons, a kind of protein discovered in 1957, capable of inhibiting viral replication, are produced by animals and man, as well as by cultured cells, as a response to viral infection or some other inductor. Interferon is more effective as an antiviral substance in the cells of the same species. In contrast, the interferon activity is not specific for a certain virus. The interferon produced as a response to a virus or to another inductor, effectively inhibits the replication of a wide variety of viruses. When the interferon is added to the cells before the infection take place, there is a notable inhibition of viral replication, while the cell function remain normal.

Viral infections in man may also be associated with complications during serious surgical operations as in gastrointestinal surgery, or in patients having a high risk of infection at the site of the operation as in cardiovascular surgery.

In aseptic surgical operations such as abdominal or cardiovascular surgery, the so-called post-operational acute phase reaction is characterized by a deterioration of the phagocytic function, a reduction of the lymphocyte response to polyclonal activators and an altered function of B cells (D. Berger, Journal of Endotoxin Research, Vol. 4 No. 1 (1997). This phase is characterized by an immunological dysfunction of the patient. The pneumonia produced by the cytomegalovirus (CMV) is more important in persons having an immune deficiency, such as patients treated with immuno-suppressors as a result of an organ transplant or a malignant process, as well as persons with natural immunologic deficiencies such as hypogammaglobulinemia and with weakening chronical processes, for which reason a pneumonia produced by CMV may be a complication in any patient with a decreased immunological capacity. Pneumonias of viral origin, do not respond to antimicrobial treatment. The pneumonia produced by the grippe virus generally affects elderly persons that are immunologically depressed due to underlying non-infectious diseases, as for example, lung, cardiovascular or kidney diseases. In all these cases it would be very useful to count on an agent with antiviral and/or immune system stimulating properties.

This invention is particularly important in the medical field. The effectiveness of the peptide disclosed herein is related to the antiviral and antibacterial effects, furthermore to activate the immune system and protect the host against bacterial or viral infectious. Thus, the peptide$_{31-52}$ (SEQ ID NO: 1) from Limulus anti-LPS factor is useful in the treatment and/or prophylaxis of both viral and bacterial infectious diseases, patients who are at a heightened risk of infection due to imminent surgery, injury, illness, or other such condition which deleteriously affects the immune system. The peptide is also useful in the treatment of immumosuppressed patients. Take together, the peptide of this invention can be considered as a new immunomodulatory agent of the immune system with a broad spectrum for the treatment of infectious diseases.

DETAILED DESCRIPTION OF INVENTION

The invention relates to a peptide comprising the amino acids$_{31-52}$ (SEQ ID NO: 1) from Limulus anti-LPS factor protein isolate from a horseshoe crab such as *Limulus polyphemus* which enhance a host's immune defense mechanisms to infection but not induce an inflammatory response.

This peptide has been shown to have an antiviral effect to protect the cells against the viral infection in vitro assay. Furthermore, supernatant from human mononuclear cells incubated with the peptide contain certain soluble mediator (s), such as IFN-γ, able to confer protection to the cells Hep-2 against future viral infections. Another hand, this peptide protects against a direct infection in vivo. These advantageous properties make the peptide of this invention useful in the prevention and treatment of infections because they selectively activate only those components of the immune system responsible for the initial response to infection, without stimulating the release of certain biochemical mediators that can cause adverse side effects. The peptide also lacks the toxicity common to many immuno-modulators.

The peptide of this invention is synthesized using a solid phase procedure. Crude peptide was extracted with a 30% acetic acid solution in water, lyophilized and then purified by RP-HPLC. Molecular mass of purified peptide was verified using a JEOL JMS-HX110HF two sector mass spectrometer equipped with a FAB gun. The resulting preparation is non-antigenic, non-pyrogenic and is pharmaceutically acceptable for administration to animals and humans.

The peptide comprising the amino acids31-52 (SEQ ID NO: 1) from Limulus anti-LPS factor protein of this invention can be used as safe, effective, therapeutic and/or prophylactic agents, either alone or as adjuvants, to enhance the immune response in humans and animals. The peptide comprising the amino acids sequences disclosed herein selectively activate only those components that are responsible for the initial response to infection caused both bacterial or viral pathogens, without stimulating or priming the immune system to release certain biochemical mediators (e.g., TNF, IL-1) that can cause adverse side effects. As such, the present peptide can be used to prevent or treat infectious diseases caused both bacterial or viral pathogens in malnourished patients, patients undergoing surgery and bone marrow transplants, patients undergoing chemotherapy or radiotherapy, neutropenic patients, HIV-infected patients, trauma patients, bum patients, patients with chronic or resistant infections, all of who may have weakened immune systems. An immunocompromised individual is generally defined as a person who exhibits an attenuated or reduced ability to mount a normal cellular and/or humoral defense to challenge by infectious agents, e.g., viruses, bacteria, fungi and protozoa. A protein malnourished individual is generally defined as a person who has a serum albumin level of less than about 3.2 grams per deciliter (g/dl) and/or unintentional weight loss of greater than 10% of usual body weight.

More particularly, the method of the invention can be used to therapeutically or prophylactically treat animals or human who are at a heightened risk of infection due to imminent surgery, injury, illness, radiation or chemotherapy, or other such condition which deleteriously affects the immune system. The method is useful to treat patients who have a disease or disorder which causes the normal metabolic immune response to be reduced or depressed, such as HIV infection (AIDS). For example, the method can be used to pre-initiate the metabolic immune response in patients who are undergoing chemotherapy or radiation therapy, or who are at a heightened risk for developing secondary infections or post-operative complications because of a diseases, disorder or treatment resulting in a reduced ability to mobilize the body's normal metabolic responses to infection. Treatment with the peptide has been shown to be particularly effective in mobilizing the host's normal immune defenses, thereby engendering a measure of protection from infection in the treated host. It may be used in elderly persons, immunologically depressed by non infectious diseases as cardiovascular or chronical diseases. It is known that these persons are susceptible to viral pneumonia e.g. the grippe virus. It may also be effective in the treatment of pneumonia due cytomegalovirus (CMV), which are more important every day in persons having immunity deficiency, e.g. persons treated with immuno-suppressors as a result of an organ transplant. The treatment with this peptide could be particularly attractive in strengthening the immune response in patients with trauma or it may be administered during the so called post-operational acute phase, where viral infections are generally associated producing severe consequences, where the patients do not respond to the antimicrobial treatments. Both in persons with traumas, as during the acute post-operational phase, there is a deterioration of the immune response given mainly by a decrease of the activity of the macrophages and their inability to respond adequately during an infection (Berger et al., Clin. Chem. Acta. 1995, Vol. 239: 121–130. Therefore, the agents that stimulate the function of the macrophages, as the main mediators of the immune response, would be of great therapeutic and prophylactic value in infectious diseases of viral or bacterial origin. The treatment with the peptide has demonstrated that it is particularly effective in mobilizing the normal immune defenses of the host, producing an increase in the protection of the host to the infection.

In another embodiment the peptide of the invention can be administrate to patients' undergoing "immunoparalysis" (Randow et al. , J. Exp. Med. 1995, Vol. 181: 1887–1892.), defined as the reduction of the monocytic MHC class II, impaired monocytic antigen-presenting activity and their diminished ability to produce inflammatory cytokines. This phenomenon is called Compensatory Anti-inflammatory Responses Syndrome (CARS). During the late hypoinflammatory phase in sepsis monocytic stimulation is useful because restitute the deficient phenotype and function of monocytes from patients with "immunoparalysis".

The present peptide is generally administered to an animal or human in an amount sufficient to produce immune system enhancement. The mode of administration of the peptide can be oral, enteral, parenteral, intravenous, subcutaneous, intraperitoneal, or intramuscular. The form in which the composition will be administered (e.g., tablet, capsule, solution, emulsion) will depend upon the route by which it is administered. The quantity of the composition to be administered will be determined on an individual basis, and will be based at least in part on consideration of the severity of infection or injury in the patient, the patient's conditions or overall health, the patient's weight and the time available before surgery, chemotherapy or other high-risk treatment. In general, a single dose will preferably contain approximately 5 mg to 10 mg of peptide per kilogram of body weight. In general, the composition of the present invention can be administrated to an individual periodically as necessary to stimulate the individual's immune response.

An individual skilled in the medical arts will be able to determined the length of time during which the composition is administrated and the dosage, depending upon the physical condition of the patient and the disease or disorder being treated. As stated above, the composition may also be used as a preventative treatment to pre-initiate the normal metabolic defenses, which the body mobilizes against infections.

The peptide can be used for the prevention and treatment of infections caused by a broad spectrum of bacterial, fungal, viral and protozoan pathogens. The prophylactic administration of peptide to a person undergoing surgery, either preoperatively, intraoperatively and/or postoperatively, will reduce the incidence and severity of postoperative infections in both normal and high-risk patients. For example, in patients undergoing surgical procedures that are classified as contaminated or potentially contaminated (e.g., gastrointestinal surgery, hysterectomy, cesarean section, transurethral prostatectomy) and in patients in whom infection at the operative site would present a serious risk (e.g., prosthetic arthroplasty, cardiovascular surgery), concurrent initial therapy with an appropriate antibacterial agent and the present peptide preparation will reduce the incidence and severity of infectious complications.

In patients who are immunosuppressed, not only by disease (e.g., cancer, AIDS) but by courses of chemotherapy and/or radiotherapy, the prophylactic administration of the peptide preparation will be reduce the incidence of infections caused by a broad spectrum of opportunistic pathogens including many unusual bacteria, fungi and viruses.

In high risk patients (e.g., over age 65, diabetics, patients having cancer, malnutrition, renal disease, emphysema, dehydration, restricted mobility, etc.) hospitalization frequently is associated with a high incidence of serious nosocomial infection. Treatment with this peptide preparation may be started empirically before characterization, use of respirators, drainage tubes, intensive care units, prolonged hospitalizations, etc. to help prevent the infections that are commonly associated with these procedures. Concurrent therapy with antimicrobial agents and the peptide preparation is indicated for the treatment of chronic, severe, refractory, complex and difficult to treat infections.

The compositions administered in the method of the present invention can optionally include other components, in addition to the peptide. The other components that can be included in a particular composition are determined primarily by the manner in which the composition is to be administered. For example, a composition to be administered orally in tablet form can include, in addition to peptide, a filler (e g., lactose) a binder (e.g., carboxymethyl cellulose, gum arabic, gelatin), an adjuvant, a flavoring agent, a coloring agent and a coating material (e.g., wax or plasticizer). A composition to be administered in liquid form can include peptide and, optionally, an emulsifying agent, a flavoring agent and/or a coloring agent. A composition for parenteral administration can be mixed, dissolved or emulsified in water, sterile saline, PBS, dextrose or other biologically acceptable carrier. A composition for topical administration can be formulated into a gel, ointment, lotion, cream or other form in which the composition is capable of coating the side to be treated, e.g., wound site.

Compositions comprising peptide preparation can be administered topically to a wound site to stimulated and enhance wound healing and repair. Wounds due to ulcers, acne, viral infections, fungal infections or periodontal disease, among other, can be treated according to the methods of this invention to accelerate the healing process. Alternatively, peptide preparation can be injected into wound or afflicted area. In addition to wound repair, the composition can be used to treat infection associated therewith or the causative agents that result in the wound. A composition for topical administration can be formulated into a gel, ointment, lotion, cream or other form in which the composition is capable of coating the site to be treated, e.g., wound site. A typical dosage for wound will be from about 5 mg to about 10 mg.

In another embodiment this invention relates to hybrid polypeptides containing the mentioned peptide sequences wherein the preferred peptide sequences constitutes the N-terminus or the C-termninus of larger polypeptide chains in a way that maintain its ability to enhance the immune response and confers this ability to the hybrid polypeptide. One preferred hybrid polypeptide comprises a fusion of any of the preferred peptides and heavy chain regions of IgG.

This invention also relates to scaffold proteins that properly exposed of the mentioned peptide sequences in such a way that maintains or enhances their ability to enhance the immune response and confers this ability to the hybrid polypeptide. The term "scaffold proteins" as used herein refers to hybrid polypeptides, which include within their polypeptide chain one or more of the selected LALF sequences in a such a way that the inserted segment forms an exposed loop in the structure of the fused protein, or polypeptide.

Peptide half life in vivo and other pharmacological parameters could be improved with hybrid and scaffold polypeptides and proteins including the preferred peptide sequence. Also DNA sequences encoding the peptides, or encoding hybrid or scaffold proteins containing the peptide sequence could be inserted in proper vectors to be expressed in vivo for therapeutic purposes along with appropriated carriers, diluents, adjuvant or stabilizing solutions or chemicals.

The novel immunological activity from Limulus anti-LPS factor peptide disclosed herein enhances the non-specific defenses of mammalian mononuclear cells and significantly increases their ability to respond to an infectious challenge. In another hand, it does not result in increased body temperatures (e.g., fever) as has been reported with many non-specific stimulants of those defenses. This critical advantage of peptide preparation may lie in the natural profile of responses it mediates in white blood cells. It has been shown that the effect of the present invention selectively activates immune responses but does not directly stimulate or prime cytokine (e g., TNF) release from mononuclear cells, thus distinguishing from other immunostimulants.

The invention is below illustrated with specific examples, which are presented with the aim of illustration, but do not limit the extent of the invention.

EXAMPLES

Example 1

Antiviral Effect of Peptide on the Cell Line HEP-2

Determination of the antiviral activity was estimated by means of the inhibition of the cytopathic effect produced by a virus on cell line Hep-2, it is a common procedure for determine antiviral activity of interferons ((Famillietti et al., 1981, Methods in Enzymology, Vol. 78: 387–396). For this purpose 96 well plastic culture dishes (Nunc, Denmark) were used. $1 \times 10^5$ cell/well in MEM medium supplemented with 10% fetal calf serum were growth up to monolayer formation (24 h). The next day 100 ul of serial dilution's of the samples containing quantities of 14 and 28 $\mu g/ml$ of different peptide from LPS-binding proteins: Limulus anti-LPS factor$_{31-52}$ (LALF), Lipopolysaccharide Binding Protein$_{86-98}$ (LBP), 18 kDa Cationic Antimicrobial Protein$_{108-128}$ (CAP-18) and Bactericidal Permeability Increasing Protein$_{86-99}$ (BPI), were incubated with the cells for 24 h. Then the cells were washed with saline solution and infected with $10^{-7}$ pfu of Mengo virus, provide by Institute of Molecular Biology, University of Zurich, which is multiplied in the cell line L929 murine fibroblasts. 18 h later degree of cell destruction was measured by fixation and staining, generally with crystal violet, for reading of cytophatic effect was used a photometer Ultramicroanalytical System (SUMA). A computer program in Pascal UCSD language for the microcomputer system was developed for all calculations and corrections (Ferrero et al., 1994, Biotecnologia Aplicada. Vol. 1:). In this case serial dilution's of human γ-IFN 70 000 IU/ml (MRI, Freeze-dried Reference Human Recombinant Gamma Interferon) was used as standard in order to define unit of antiviral activity. For this reason the antiviral protection shown by the peptide is related to International Units of γ-IFN (Ul/ml). As a negative control were used different peptides from proteins that bind endotoxin. LPS at 10 ng/ml was used as a positively control because is well known that it induced the production of IFNs (Manthey et al., 1994, J. Immunology. Vol. 153: 2653–2663). One unit of antiviral activity is define as the quantity of IFN able to produce an 50% inhibition of the viral replication.

The results are shown in Table 1.

TABLE 1

Antiviral effect shown by different peptide from LPS-binding proteins on the cell line Hep - 2

| Peptide | Conc. µg/ml | Antiviral effect IU/ml γ-IFN | | | Mean ± SD | |
|---|---|---|---|---|---|---|
| | | 1 | 2 | 3 | | |
| LALF | 14 µg/ml | 35 | 31.7 | 22 | 29.5 | 6.75 |
| | 28 µg/ml | 28.7 | 27 | 31.4 | 28.3 | 3.21 |
| LBP | 14 µg/ml | 13 | 10 | 12.5 | 11.8 | 1.60 |
| | 28 µg/ml | 10 | 9.3 | 9 | 9.4 | 0.51 |
| BPI | 14 µg/ml | 8 | 8.7 | 10 | 8.9 | 0.25 |
| | 28 µg/ml | 10 | 10.4 | 12.4 | 10 | 1.84 |
| CAP-18 | 14 µg/ml | 9 | 8.7 | 9.2 | 8.9 | 1 |
| | 28 µg/ml | 12.2 | 9 | 9 | 10.9 | 1.22 |
| LPS | 0.01 µg/ml | 20.7 | 30 | 31.2 | 27.3 | 5.74 |
| Cells alone | | 8.3 | 9 | 11 | 9.4 | 1.40 |

Table 1 shows that only the peptide LALF is able to induce an antiviral state in the cells Hep-2 defined as International Units/ml of γ-IFN. There was no effect for the other peptides derive from LPS-binding protein.

Example 2

Antiviral Effect of Peptide on the Cell Line MDBK

Determination of the antiviral activity was estimate by means of the inhibition of the cytopathic effect produced by a virus on cell line MDBK, essentially as is described in the example 1. The cells used in this approach were MDBK a kidney normal bovine cells line [ATCC No. 6071], which are infected with $10^{-7}$ pfu of bovine enterovirus. Increasing quantities of LALF peptide were used in order to induced protection in the-cells: 10 µM, 20 µM and 40 µM. In this case serial dilution's of human α-IFN 70 000 IU/ml (MRI, Freeze-dried Reference Human Recombinant Alpha Interferon) was used as standard in order to define unit of antiviral activity. One unit of antiviral activity is defining as the quantity of IFN able to produce a 50% inhibition of the viral replication. The FIG. 5 shows that LALF peptide is able to induce protection in the cell line MDBK in a doses dependent manner.

Example 3

Supernatant From Human Mononuclear Cells Stimulated With Peptide Limulus Anti-LPS Factor$_{31-52}$ LALF) Induce Antiviral Effect on HEP-2 Cell Line Venous blood was obtained from healthy volunteers and Ficoll-Hypaque centrifugation, fractionated mononuclear cells. The mononuclear cells were washed and resuspended in endotoxin-free RPMI-1640 culture medium supplemented with 10% fetal calf serum. Concentration of $2 \times 10^6$ cells/ml were aliquoted into 24-well microtiter plates (Nunc, Denmark). The cells were then incubated with 14 and 28 µg/ml of different peptides: Limulus anti-LPS factor$_{31-52}$ (LALF), Lipopolysaccharide Binding Protein$_{86-99}$ (LBP) and 18 kDa Cationic Antimicrobial Protein$_{108-128}$ (CAP-18), at 37° C. for 18 hours in 5% $CO_2$. The cells were centrifuged at 3000 rpm for 5 min and then serial dilutions of supernatants were assays for antiviral activity using the procedures described in the example 2.

The results are summarized in Table 2. Only LALF peptide used as stimulant of human peripheral blood mononuclear cells induce them to release certain mediator capable of conferring protection to the Hep-2 cells against viral infections.

TABLE 2

Supernatant from human mononuclear cells stimulated with LALF peptide is able to induce an antiviral state on Hep - 2 cell line

| Peptide | Conc. μg/ml | Antiviral effect IU/ml γ-IFN | | | | |
|---|---|---|---|---|---|---|
| | | 1 | 2 | 3 | Mean | ± SD |
| LALF | 14 μg/ml | 28 | 27.6 | 20.4 | 25.3 | 4.27 |
| | 28 μg/ml | 28.4 | 28 | 20 | 25.4 | 4.73 |
| LBP | 14 μg/ml | 7 | 7.4 | 9.8 | 8.0 | 1.51 |
| | 28 μg/ml | 7.3 | 9 | 7.4 | 7.9 | 0.95 |
| CAP-18 | 14 μg/ml | 7.8 | 8 | 11 | 8.93 | 1.79 |
| | 28 μg/ml | 8.2 | 9 | 9.6 | 8.93 | 0.70 |
| LPS | 0.01 μg/ml | 23 | 20 | 28.8 | 23.9 | 4.47 |
| monocytes alone | | 12.6 | 9.2 | 8 | 9.9 | 2.38 |

Example 4

Lack of in Vitro Stimulation of TNFα From Human Mononuclear Cells Incubated With Peptide Venous blood was obtained from healthy volunteers and Ficoll-Hypaque centrifugation, fractionated mononuclear cells. The mononuclear cells were washed and resuspended in endotoxic-free RPMI 1640 medium supplemented with 10% fetal calf serum. 30×10$^6$ cells were aliquoted into plates p-60 (Nunc, Denmark). The cells were incubated with 14 or 28 μg/ml LALF at 37° C. for 18 hours in 5% $CO_2$ and then centrifuged at 3000 rpm during 5 min. The synthesis of TNFα in the supernatant was determined by specific enzyme-linked immunoadsorbent assay (ELISA), kindly provided by Dr. W. Buurman (University Hospital Maastrich, The Netherlands). The results are summarized in Table 3. LALF peptide used as a stimulant at doses of 14–28 μg/ml alone did not induce increased levels of TNF-α over the control buffer treated cells.

TABLE 3

TNF - α synthesis by human mononuclear cells stimulated with various peptides from LPS-binding proteins

| Peptide | Conc. μg/ml | TNF - α (ng/ml)[1] |
|---|---|---|
| LALF | 14 μg/ml | 0.84 |
| | 28 μg/ml | 0.80 |
| LBP | 14 μg/ml | 0.80 |
| | 28 μg/ml | 0.78 |
| CAP-18 | 14 μg/ml | 0.76 |
| | 28 μg/ml | 0.75 |
| LPS | 0.01 μg/ml | 2.20 |
| monocytes only | | 0.75 |

[1]The values are the mean of three donors.

Example 5

In Vivo Protection Against Infection in Mice

A model of fulminating Gram-negative peritoneal sepsis was developed in mice BalB/c to characterize the efficacy of LALF peptide in protecting an immunologically intact host against serious infections. Groups of mice received LALF peptide (14 μg/0.1 ml) or saline control (0.1 ml) intraperitoneally 20 hours prior to infectious challenge. A doses of *Pseudomona aerukinosa* ($2 \times 10^8$ bacterial/mice) producing a total mortality of approximately 90% (Browder et al., 1987, Surgery. Vol. 102: 206–214) was used in order to induce an experimental peritonitis. Survivor's mice were counted each 24 hours during 120 hours after bacterial challenge. Survival data were analyzed by statistical test Kaplan-Meyer, the significance analysis was determined using a long-rank test, table 5. Blood was collected for TNF quantification from the retroorbital sinus at the time 0, 20, 40, 60, 90, 120, 180, 240 min in the control group and peptide treated-mice. The concentration of TNF-α in mouse serum was determined using a specific ELISA kindly provided by. Dr. W. Buurman (University Hospital Maastrich, The Netherlands). FIG. 4.

TABLE 4

Prophylactic effect of LALF peptide on survival in a mice model of Gram - negative peritoneal sepsis

| Group | Survival (%) | P vs. Saline |
|---|---|---|
| Saline Sol. | 8% | |
| LALF peptide prophylac. | 36% | P < 0.0098 |

The peptide protects mice from lethal bacterial challenge when it is administrated prophylactically. The observed protection is attribute to a regulatory activity of peptide on the immune response of the host. This effect induced a decrease of the proinflammatory cytokine TNF FIG. 4. This capacity may attenuate the lethal effect observed during the sepsis as a consequent of the systemic proinflammatory mediator releases.

Example 6

Lalf Peptide is Not Toxic and Does Not Affect the Levels of TNF-α in Vivo

This approach was developed in mice BalB/c between 6–8 old. The mice were injected intravenously with 50 μg of peptide in 0.1 ml [2.5 mg/kg of body weight] or saline solution as a control. The behavior of animals was observed each 4 hours during 24 h. Survival was followed for one week. Blood was collected for TNF-α quantification from the retroorbital sinus at the time 0 h. 6 h, 24 h and 48 h in the control group and peptide treated-mice. The concentration of TNF-α in mouse serum was determined using a specific ELISA kindly provided by Dr. W. Buurman (University Hospital Maastrich, The Netherlands). All mice [10 animals/group] survivor beyond of one week. LALF peptide is not toxic in vivo and does not stimulate TNF-α production, FIG. 3.

Example 7

Regulation Effect of Lalf-derived Peptide on Immune Response in activated-peritoneal Macrophages Peritoneal elicited cells were obtained from Balb/c mice (CENPALAB, Havana, Cuba). Primary mouse macrophages was collected from the peritoneal cavity 4 days after intraperitoneal injection with 1 ml of 4% Brewer's thioglicollate broth. Cell were maintained in RPMI 1640 supplemented with 10% heat-inactivated fetal bovine serum, 2 mM L-glutamine, 200 units/ml penicillin, and 200 μg/ml streptomycin at 37° C. in 5% $CO_2$/96% air.

Assay for Secretion of $NO_2$-(Jin, F[29], Nathan, C, Radzioch, 0, and Ding, A. Cell, 1997, 88: 417–426). Cells were plated in 96-well plates at 2×10⁶ cells/ml in 200 μl of medium and incubated at 37° C. for 2 h, then non-adherent cells were removed by repeated washing with PBS. Macrophage were pre-incubated with 5 μM of LALF peptide during 18 h, afterward were washed with RPMI medium in order to eliminated the peptide. Then the macrophages were treated 72 hr with LPS of *E. coli* 0111:B4, Sigma (1 μg/ml). Cell viability was assessed by mitochondrial-dependent reduction of MTT to formazan (Szabo[30], c, Mitchell, J A, Gross, S S, Thiemermann, C, and Vane, JR. J. Pharm. Exp. Therap., 1992, 265: 674–80). 50 μl of cultured medium was mixed with equal volume of Greiss's reagent (1% sulfanilamide, 0.1% naphthylethylenediamine dihydrochloride, 2.5% $H_3PO_4$). Absorbance at 540 nm was recorded in a microplate reader (SUMA) with sodium nitrite as standards (Green[28], L C, Wagner, D A, Glogowski, J, et al. Anal Biochem 1982; 126: 131–8). Nitrite content of similarly incubated cell-free medium was subtracted.

TNF-α assay: Cells were plated in 96-well plates at 2×10⁶ cells/ml in 200 μl of medium and incubated at 37° C. for 2 h. Non-adherent cells were removed by repeated washing with PBS. Macrophages were pre-incubated with 5 μM of LALF peptide during 18 h, afterward were washed with RPMI medium in order to eliminate the peptide. Then macrophages were treated with LPS of *E. coli* 0111:B4, Sigma (1 μg/ml). TNF-α was determined in supernatants from cultured cells at the time 1 h, 2 h, 4 h, 6 h and 24 h used a kit of ELISA kindly provided by [Dr. W. Buurman Univ. Hosp. Maastrich, Netherlands].

As shows the FIG. 6 the TNF levels were down regulated in macrophages-treated peptide. On contrary NO production was up regulated, FIG. 7. The viability of the cells did not affect during the assay. The viability was never found lower than 98%.

It seems to be a preferring and specifically modulation of LPS-induced response. Take together, may be the peptide mediate some kind interaction with the immune system cells and lead to immunoregulatory effect able to enhance and/or modulate the immune response in the host.

EXAMPLE 8

Stimulation of PBMCs With LALf-derived Peptide. Analysis of Cytokine Gene Expression Using The Ribonuclease Protection Assay (RPA)

The Ribonuclease Protection Assay (RPA) is a highly sensitive and specific method for the detection, quantification and characterization of RNA molecules (Gilman[32], M. In Current Protocols in Molecular Biology. J. Wiley and Sons, New York, p. 4.7.1–7.7.8. 1988 and Dent[33], A. L., Shaffer, A. L., Yu X., Allman, D., Staudt, L. M., 1997. Cytokine expression and germinal center formation by Bcl-2. Science. 276: 589–592). Samples of total RNA from stimulated and nonstimulated human PBMCs were analyzed for distinct mRNA species by PharMingen's RiboQuant™. Multi-Probe Ribonuclease Protection Assay System with the hck-1 probe template set (Cat. No. 45031P) which including mRNA species analyses for a different cytokine eg. (IL-5, IL-4, IL-10, IL-15, IL-9, IL-2, IL-13, IFN-γ).

Briefly, a high specific activity, [³²P]-labeled anti-sense cytokine RNA probe set [hck-1, Cat.No.45031P] is hybridized in excess to samples target RNA from PBMCs incubated with 5 μM of the peptide for 18 hours. Free probe and other single stranded RNA molecules are digested with Rnases, whereas annealed probe: target RNA duplexes are protected from RNase digestion. These remaining Rnase-protected probes are purified, resolved on denaturing polyacrylamide gels according to their size, and imaged by autoradiography. The identity and quantity of each mRNA species in the original RNA sample can then be determined based on the signal intensities given by the appropriately sized of protected probe fragment bands. Unprotected probe set and a probe for housekeeping gene transcripts are incorporating in order to identify and quantify the RNA molecules in the original samples. For furthermore specificities see Hot-Lines (PharMingen) Vol.3, No.1 pp.1 1997 or PharMingen RiboQuant™ Multi-Probe Rnase Protection Assay System, Instruction Manual 4th Edition, August 1997.

Total RNA was obtained using a Single-Step Method of RNA isolation by AGPC Extraction (Chomczynski[34] et al. 1987, Analytical Biochemistry. Vol. 162: 156–159).

As shows the FIG. 8 the peptide is able to preferentially induce IFN-γ, IL-2 and IL-13 gene expression in human PBMCs. Expression and subsequent release of IFN-γ might be the responsible of the antiviral property observed in supernatants from PBMCs incubated with the peptide. Furthermore, this typically Th-1 response characterized by production of IL-2 and IFN-γ may correlated with the protect effect of the peptide during P. aeruginosa infection in mice. Because, has been reported that IFN-γ decreases the inflammatory response in chronic P. aeruginosa infection in rats (H. K. Johansen[35], H. P. Hougen, J. Rygaard and N. Hoiby. Clin. Exp. Immnunol. 1996, 103: 212–218.). Besides, have been found that treatment with IFN-.gamma. influence the cell-mediated response and therapeutic potential has been demonstrated in vivo against *Cryptococcus neoformans* (Joly[36] V, Saint-Julien L. Carbon C, Yeni P. Journal of Infect. Dis. 1994; 170: 1331–4), *Toxoplasma gondii* (Benedetto[37] N, Auriault C, Darcy F et al. Eur Cytokine Net. 1991; 2: 107–14) and *Klebsiella pneumoniae* (Hagen[38] TLM, Vianen von W, Bakker-Woudenberg IAJM. J. Infect Dis. 1995; 171: 385–92). Here we showed that LALF-derived peptide is able to produce immune system enhancement and can be used to prevent or treat infectious diseases caused by a broad spectrum of pathogens. Furthermore, the LALF-derived peptide can be used in patients who may have a weakened immune system. Statistical methods. All values in the figures and table are expressed as mean±SD. Statistical analysis was done by using the Kruskal Wallis test. The different between groups was determined by a Dunn test. A p values less than 0.05 was assumed to be significant.

BRIEF DESCRIPTION OF THE DRAWINGS

FIG. 1: Shows the sequence of the peptide LALF (SEQ ID NO: 1) that is use to define the activity disclosed herein.

REFERENCES

Figure 2:
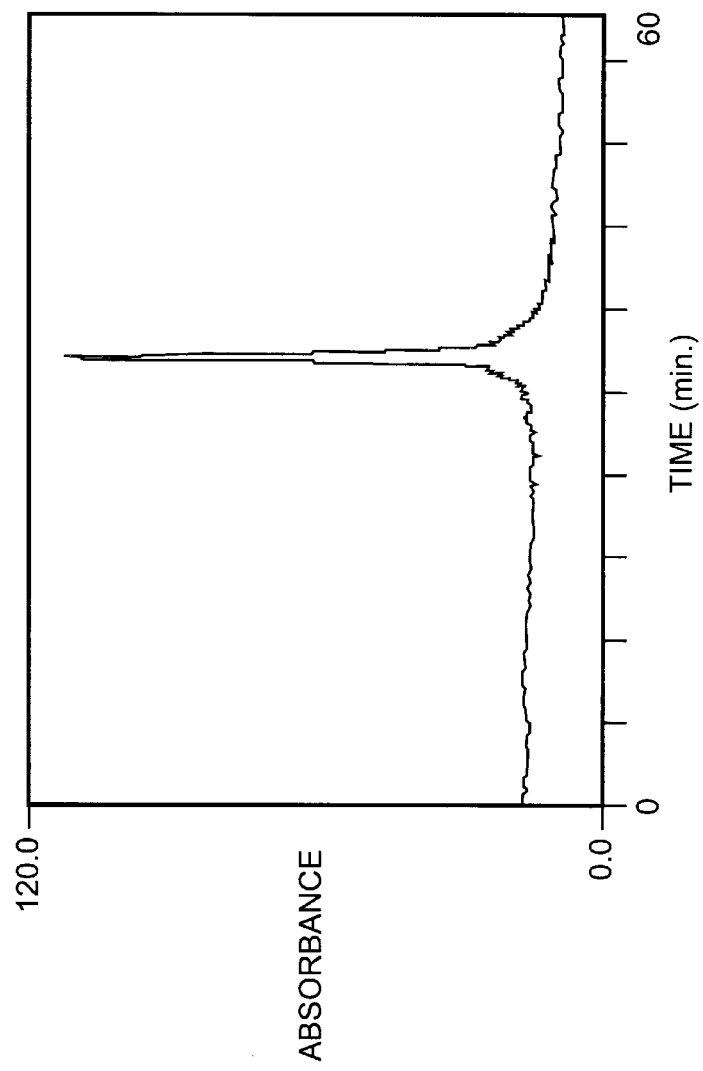
FIG. 2: Shows RP-HPLC chromatographic purification of the LALF peptide. Peak A: elution of the peptide with 98% of purity.
Figure 3:
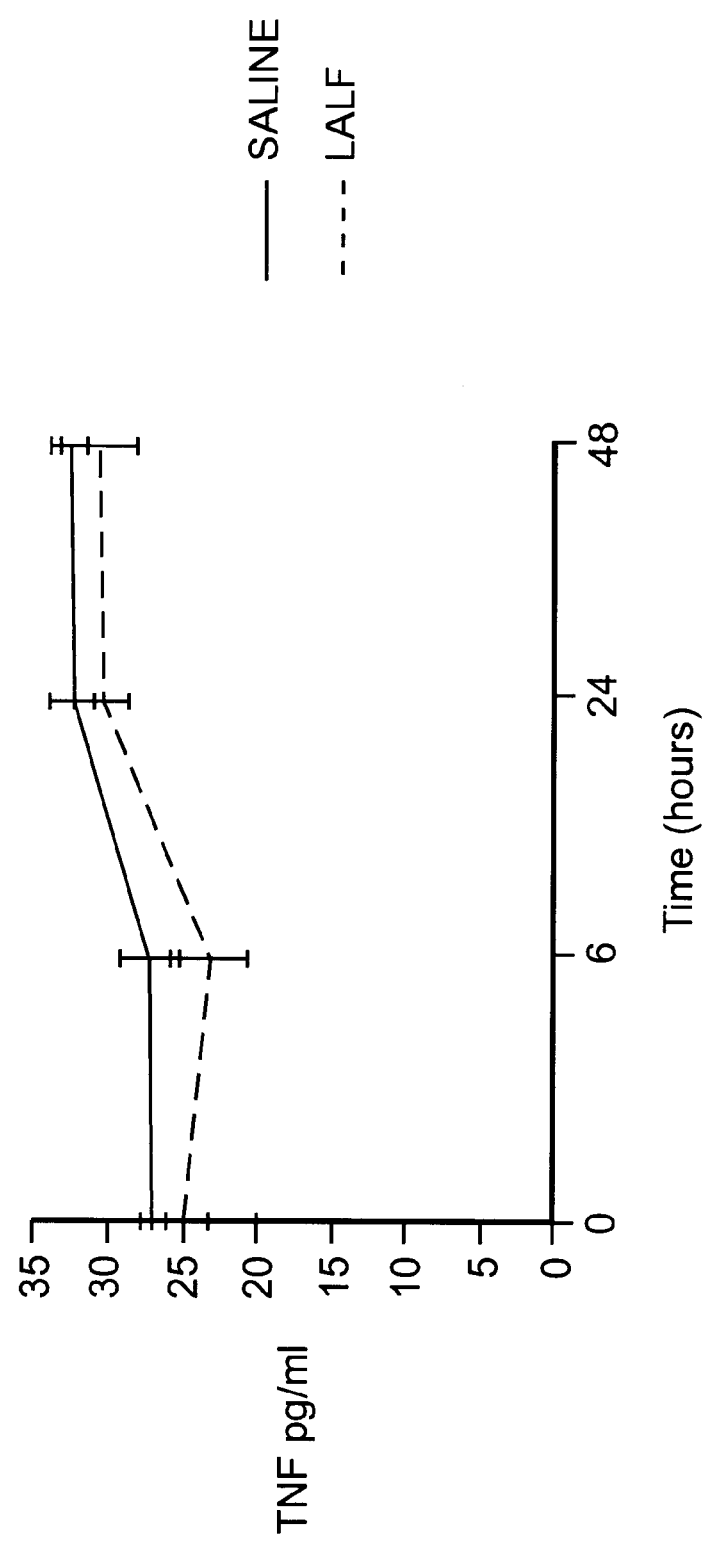
FIG. 3: Shows the change in serum TNF levels, over time, taken from mice intravenously infused with saline solution or 50 μg of LALF peptide.
Figure 4:
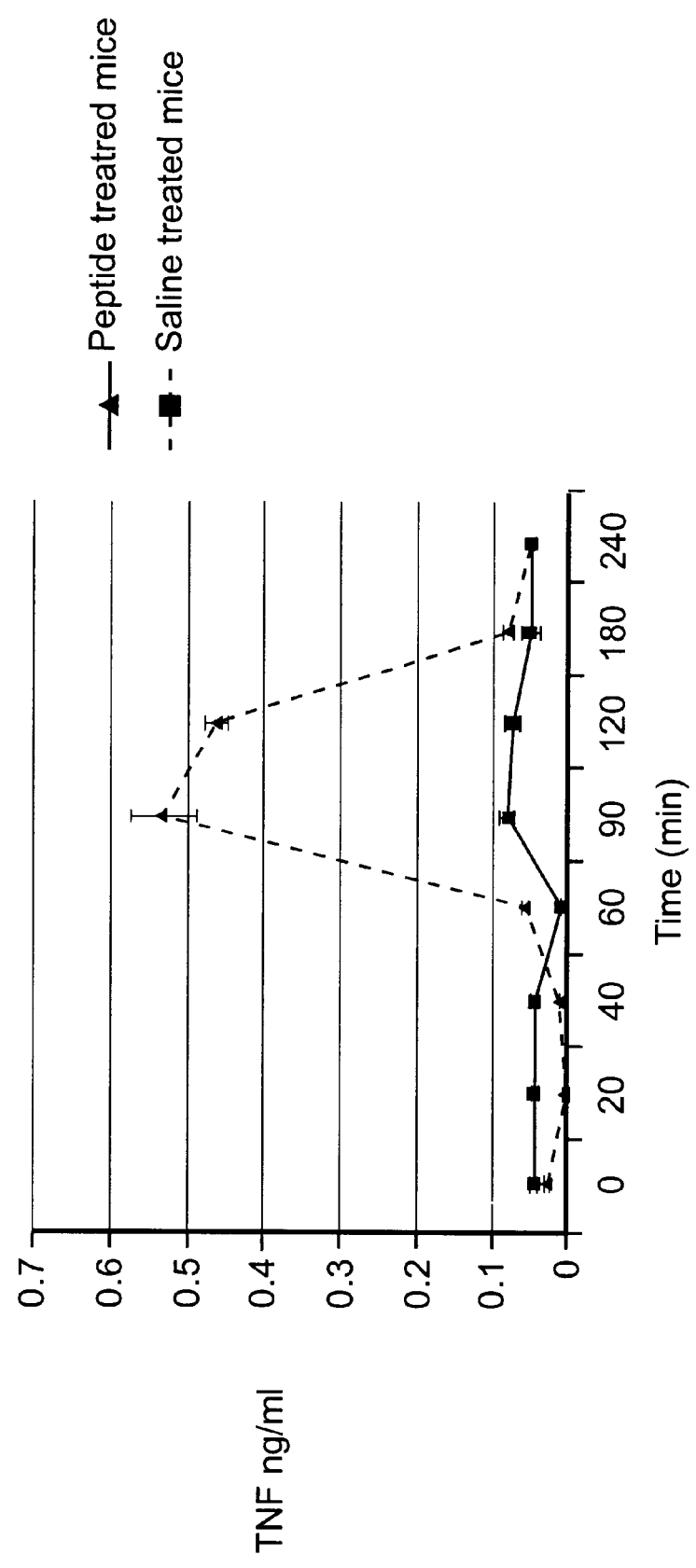
FIG. 4: Comparison of systemic levels of TNF in LALF-derived peptide treated-mice and control group. Eight-week-old mice were injected i.p. with 14 μg of peptide in 0.1 ml saline or saline alone. Twenty hours after the mice were injected i.p. with a lethal doses of *P. aeruginosa*. At 0, 20, 40, 60, 90, 120, 180 and 240 min following the challenge, the mice were bled from the retroorbital sinus and the serum concentration of TNF was measured.
Figure 5:
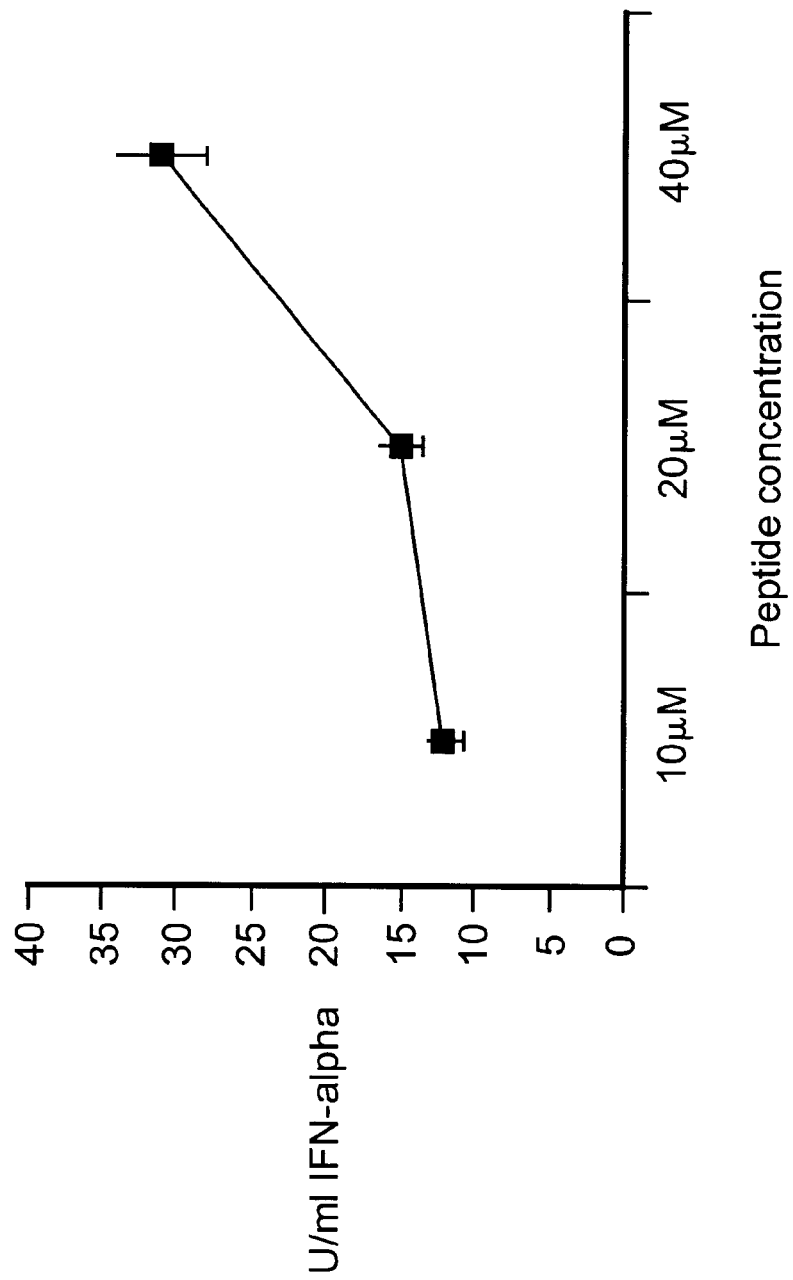
FIG. 5: Shows the antiviral properties of LALF peptide on the cell line MDBK. The cells were treated with increasing quantities of peptide during 18 hours. Afterwards, the cells were challenged with a bovine enterovirus. Antiviral activity is referred as U/ml α-IFN.
Figure 6:
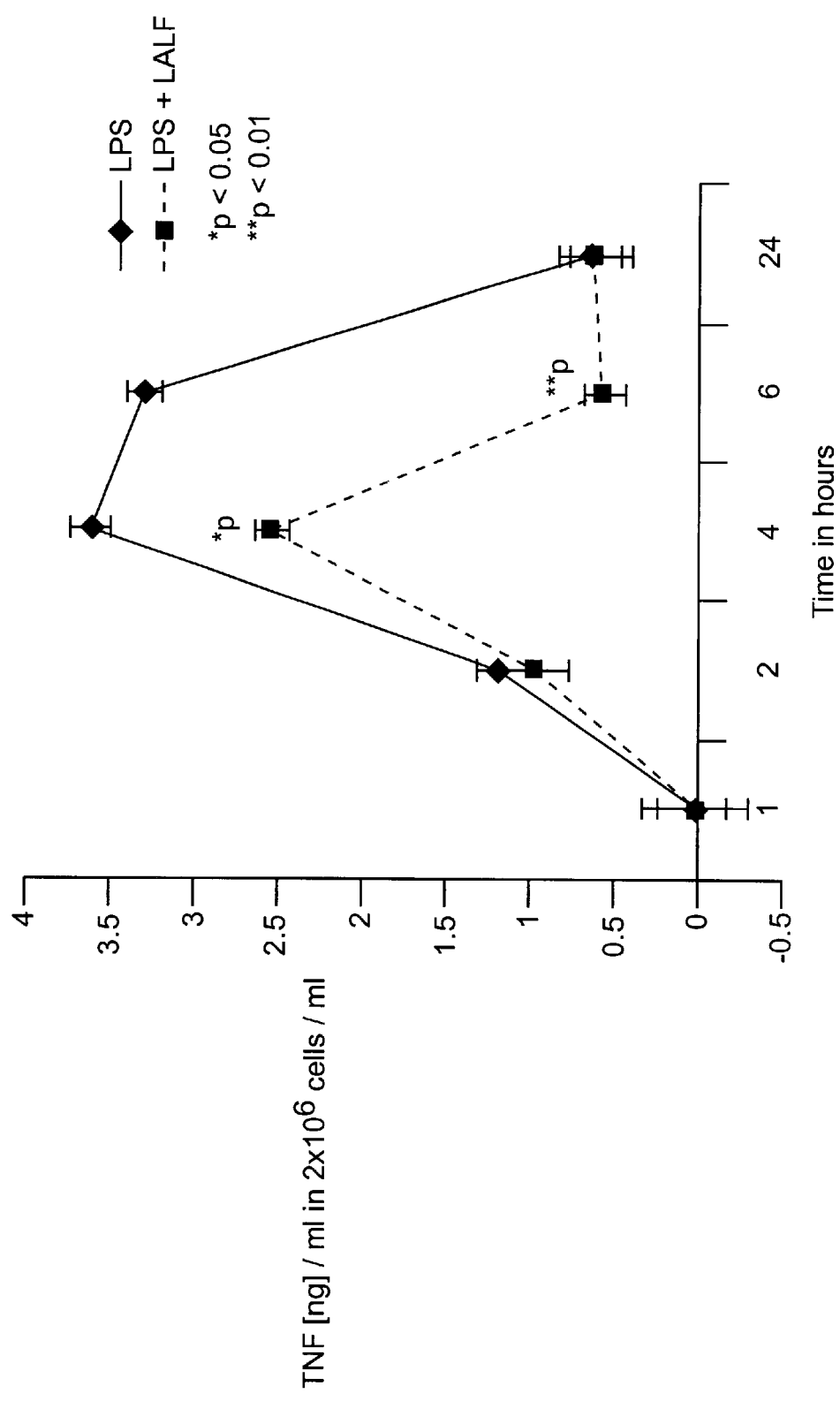
FIG. 6: Regulatory effect of LALF derived-peptide on TNF-α production in stimulated peritoneal macrophages. The macrophages were pretreated with 5 μM of LALF peptide during 18 hours and then the cells were activated with 1 μg of E. coli LPS. TNF-α was measured in the cells cultured supernatants at different time.
Figure 7:
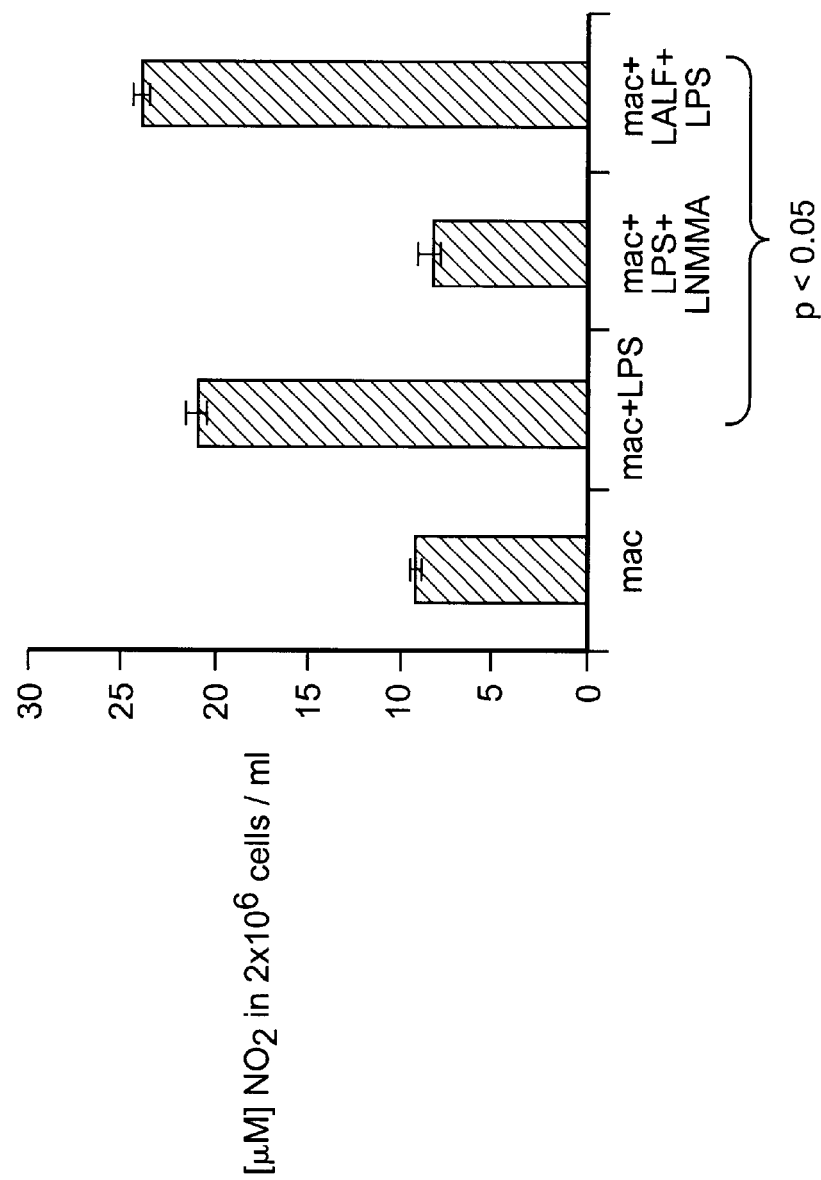
FIG. 7: Regulatory effect of LALF derived-peptide on NO production in stimulated peritoneal macrophages. The macrophages were pretreated with 5 μM of LALF peptide during 18 hours and then the cells were activated with 1 μg of E. coli LPS during 72 h. Levels of NO were measured in the cells cultured supernatants using the Greiss method.
Figure 8:
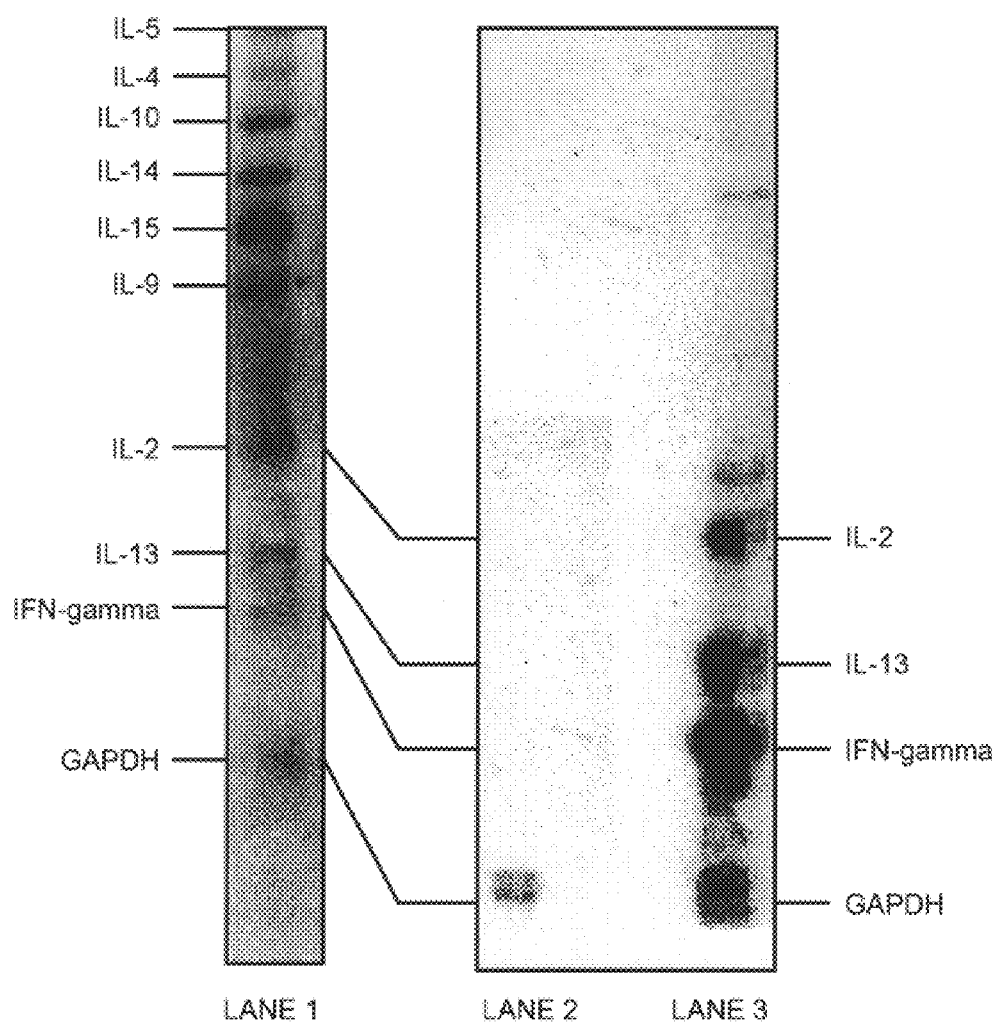
FIG 8: Samples of total RNA from stimulated human PBMCs with 5 μM of peptide for 18 hours were analyzed for distinct mRNA species by using PhaiMingens RiboQuant Multi-Probe Ribonuclease Protection Assay System with the hck-1 probe template set (Cat. No. 45031P). The autoradiogram from this analysis shows the hck-1 as an unprotected probe set (Lane 1). Also shows the corresponding RNase-protected probes following hybridization with: total RNA isolated from PBMCs nonstimulated (Lane 2) and total RNA isolated from PBMCs stimulated with 5 μM of LALF peptide during 18 hours (Lane 3).

1. Morrison and Ulevitch. Am. J. Pathol. Vol. 93: 527 (1978).
2. Bone., Annals Int. Med. Vol. 115: 457 (1991).
3. Helene et al. , Infection and Immunity. Vol. 62: 1185 (1994).
4. Schumann et al., Science, Vol. 249: 1429 (1990).
5. Wright et al., J. Exp. Med. Vol. 170: 1231 (1989).
6. Wright et al., Science. Vol. 249: 1431 (1990).
7. Wright et al. , J. Exp. Med. Vol. 173: 1281 (1991).
8. Worthen et al. J. Clin. Investig. Vol. 20: 2526 (1992).
9. Gazzano-Santoro., WO 95/00641.
10. Wainwright et al., WO 92/20715.
11. Warren et al. Infect. Immun. Vol. 60: 2506–2513 (1992).
12. Hoess et al., WO 95/05393.
13. Hoess et al., The Embo Journal. Vol.12: 3351–3356 (1993).
14. Randow et al., J. Exp. Med. Vol. 181: 1887–1892 (1995).
15. Famillietti et al. Methods in Enzymology. Vol. 78: 387–396 (1981).
16. Ferrero et al., Biotecrnologia Aplicada. Vol. 1 (1991).
17. Sheila et al. Infect and Immunity. Vol. 63; 601–608 (1995).
18. Browder et al. Surgery. Vol. 102: 206–214 (1987).
19. Berger et al, Journal of Endotoxin Research. Vol. 4: 17–24 (1997).
20. Berger et al., Clin. Chim. Acta. Vol. 239: 121–130 (1995).
21. Capodici C., Weiss J. Journal of lmmnunology. Vol.156 (12): 4789–96 (1996).
22. Taylor A H., Heavner G., Nedelman M. et al., J. Biol. Chem. Vol. 270 (30): 17934–8 (1995).
23. Garcia C., Saladino R., Thompson C. et al., Crit. Care. Med. Vol. 22 (8): 1211–8 (1994).
24. Battafaraono R. J. , Dahlberg P S., Ratz C. A. et al., Surgery Vol. 118 (2): 31824 (1995).
25. Fletcher M. A., Kloczewiak M. A., Loiselle P. M. et al., J. Infect. Dis. Vol. 175 (3): 621–32 (1997).
26. Ried C., Wahl C., Miethke T. et al. J. Biol. Chem. Vol. 271 (45): 28120–7 (1996).
27. Kloczewlak M., Black K. M., Loiselle P. et al., J. Infect. Dis. Vol. 170 (6): 1490–7 (1994).
28. Green L C. Wagner D A., Glogowski, J. et al; Anal Biochem. Vol. 126: 131–8 (1982).
29. Jin, F, Nathan, C, Radzioch, D, and Ding A. Cell Vol. 88: 417–426 (1997).
30. Szabo, c, Mitchell, J A, Gross, S S, Thiemermann, C, and Vane, J R. J. Pharm. Ex,. Therap., 1992, 265: 67480)
31. Roth R I. Su D H. Child A H. Wainwright N R and Levin J. Journal of Infectious Diseases. Vol. 177 (2): 388–394, 1998.
32. Gilman, M. In Current Protocols in Molecular Biology. J. Wiley and Sons, New York, p. 4.7.1–4.7.8. 1988.
33. Dent, A L., Shaffer, A. L, Yu X., Allman, D, Staudt, L. M., 1997.
34. Chomczynski et al. 1987, Analytical Biochemistry. Vol. 162; 156–159.
35. H. K. Johansen, H. P. Hougen, J. Rygaard and N. Hoiby. Clin. Exp. Immnunol. 1996, 103: 212–218.
36. Joly V, Saint-Julien L, Carbon C, Yeni P. Journal of Infect. Dis. 1994; 170: 1331–4.
37. Benedetto N, Aunault C, Darcy F et al. Eur Cytokine Net. 1991; 2: 107–14.
38. Hagen TLM, Vianen von W, Bakker-Woudenberg IAJM. J. Infect Dis. 1995; 171: 385–92.

What is claimed is:

1. A viral vaccine comprising a peptide or protein having the amino acid residues 31–52 (SEQ. ID NO.1) of Limulus polyphemus anti-LPS factor, wherein said peptide or protein is an adjuvant in said viral vaccine.

* * * * *

UNITED STATES PATENT AND TRADEMARK OFFICE
CERTIFICATE OF CORRECTION

PATENT NO. : 6,632,793 B1
DATED : January 23, 2004
INVENTOR(S) : Vallespi et al.

It is certified that error appears in the above-identified patent and that said Letters Patent is hereby corrected as shown below:

Column 2,
Line 30, now reads "Wright et al., *J. Exp. Med.* 173: 281 (1991),...", and should read
-- Wright et al., *J. Exp. Med.* 173: 1281 (1991),... --
Line 47, now reads "Chem. 270: 17934, (19951.", and should read
-- Chem. 270: 17934, (1995). --

Column 3,
Line 9, now reads "and has only a shart half-life in circulation.", and should read
-- and has only a short half-life in circulation. --

Column 12,
Line 9, now reads "Radzioch, 0, and Ding, A. ...", and should read
-- Radzioch, D., and Ding, A. .... --

Column 13,
Line 43, now reads "Stimulation of PBMCs With LALf-Derived Peptide.", and should read -- Stimulation of PBMCs With LALF-Derived Peptide. --

Column 15,
Line 18, now reads "by using PhaiMingens Ribo Quant ...", and should read
-- by using PharMingens Ribo Quant ... --

Signed and Sealed this

Thirtieth Day of March, 2004

JON W. DUDAS
*Acting Director of the United States Patent and Trademark Office*

SEQUENCE LISTING

```
<160> NUMBER OF SEQ ID NOS:  1

<210> SEQ ID NO 1
<211> LENGTH: 22
<212> TYPE: PRT
<213> ORGANISM: Limulus polyphemus

<400> SEQUENCE: 1

Cys His Tyr Arg Ile Lys Pro Thr Phe Arg Arg Leu Lys Trp Lys Tyr
  1               5                  10                  15

Lys Gly Lys Phe Trp Cys
             20
```